United States Patent [19]

Beckman et al.

[11] Patent Number: 5,248,616
[45] Date of Patent: Sep. 28, 1993

[54] METHOD AND APPARATUS FOR DETECTION OF AQUEOUS NITRIC OXIDE FROM BIOLOGICAL SAMPLES

[76] Inventors: Joseph S. Beckman, 4432 Briarglen Dr., Birmingham, Ala. 35243; Karl A. Conger, 2308 Blue Ridge Dr., Leeds, Ala. 35094

[21] Appl. No.: 893,451

[22] Filed: Jun. 4, 1992

[51] Int. Cl.$^5$ .................. G01N 33/00; A61B 5/00
[52] U.S. Cl. .................. 436/116; 436/53; 436/68; 436/106; 436/122; 436/178; 422/68.1; 422/82; 422/82.04; 73/19.1; 73/864.81; 128/632; 95/46; 96/6
[58] Field of Search .................. 422/68.1, 69, 81, 82, 422/82.04; 436/52, 53, 63, 68, 106, 116-118, 119, 122, 177, 178; 73/19.01, 19.1, 864.81; 128/632, 633, 635; 55/158, 159

[56] References Cited

U.S. PATENT DOCUMENTS

| | | | |
|---|---|---|---|
| 3,572,994 | 2/1968 | Hochstrasser | 436/68 |
| 3,983,864 | 10/1976 | Sielaff et al. | 128/2 G |
| 4,016,864 | 4/1977 | Sielaff et al. | 128/2 G |
| 4,187,856 | 2/1980 | Hall et al. | 128/635 |
| 4,516,580 | 5/1985 | Polanyi | 123/632 |

Primary Examiner—Jill A. Johnston
Assistant Examiner—David Redding
Attorney, Agent, or Firm—Gunn & Kuffner

[57] ABSTRACT

A method and apparatus are set forth for enhancing the concentration of oxides of nitrogen in the preferred embodiment. A permeable membrane is formed into a tube placed in a container. A sample containing bound nitrogen in placed in a container in contact with the tube. A carrier gas is swept through the tube in contact with the wall of the tube. This enables hydrophobic gases such as oxides of nitrogen to migrate through the wall of the tube and they are swept into a detection system. If desired, they can be permitted to accumulate in the wall for an interval and the carrier gas can be switched from off to on to achieve peak concentration for delivery to a bound nitrogen analytical device. Other hydrophobic gases such as oxides of sulfur can likewise be identified by sulfur analyzer. This enables an increase in trace concentration.

12 Claims, 1 Drawing Sheet

METHOD AND APPARATUS FOR DETECTION OF AQUEOUS NITRIC OXIDE FROM BIOLOGICAL SAMPLES

BACKGROUND OF THE DISCLOSURE

The measurement of extremely dilute concentrations of nitric oxide in biological samples is a significant measurement in physiological procedures. It is thought to be significant as a vasodilatory produced by endothelium. It is also an antithrombogenic agent. It is thought to be important as an agent controlling neuron level activities in the brain. It is thought to be a significant mediator of myocardial or cerebral ischemia. However, all of these processes where nitric oxide is important involve levels of nitric oxide that are quite small and are very difficult to measure in such small quantities. While nitric oxide analyzers are evidenced by a device such as that shown in the Parks patent (U.S. Pat. No. 4,018,562) it is difficult to obtain data from measuring instruments currently available because the concentrations of nitric oxide of interest to pathological conditions are such small trace quantities that measurement is difficult. Presently, there are no instruments available which necessarily provide measurements indicative of nitric oxide concentration in solution. In effect, this requires measurements at levels less than one part per billion.

The present disclosure sets forth a method of obtaining such measurements in tissue, for instance, or in aqueous solution where the nitric oxide (NO sometimes hereafter) may be present. The NO is, if present, available in such small quantities that it is normally obscured by the base line noise of the measuring systems. Even the finest of measuring system has a lower limit of sensitivity. The present disclosure sets forth a method and procedure for enhancing the sensitivity. Beyond that, it also describes a method of testing pathological fluids so that aqueous solutions of NO can be tested and the amount of NO can be measured. It is believed to be able to measure down to the range of about 1.0 nanomolar concentrations of NO in pathological fluids.

The present method contemplates the testing of a sample of some pathological fluid typically an aqueous solution which may or may not have NO in it. The solution is introduced into a container and is stirred continuously at a fixed rate. In the container, there is a tubing formed of a particular type of material. The preferred material is hydrophobic and permeable to NO. Typical permeable materials are made of propylene or perhaps fluorocarbons. Some are offered under the trademark Celgard (a trademark of Hoechst-Celanese Corp.) and others various specific Teflon models (a trademark of the DuPont firm). In addition, the DuPont product known as Nafion is quite successful in this regard. A container receives and holds the sample as it is stirred over an interval. A portion of the gases in the aqueous solution in the container will be absorbed into the wall of the tubing. The tubing is periodically swept by a carrier gas. The accumulated trace amount of nitric oxide and perhaps other trace gases will be absorbed into the wall of the tubing, and when the gas stream flows, the carrier gas will pick up the accumulated gases from the wall and carry them through the tubing. By controlling the scale factors namely the interval during which stirring occurs without carrier gas flow and then switching on the carrier gas, and by further controlling the temperature of the solution, the extent of stirring, the carrier gas flow rate and other scale factors, the NO is concentrated so that there is a peak at an NO detector downstream of the tubing whereby the peak is read and is proportional to the sample concentration. By fixing the scale factors, variations in concentration can be obtained which provide peaks substantially above the noise level at the threshold operation of the detector.

The foregoing describes some of the problems that relate to detection of nitric oxide. It is possible also to form other oxides of nitrogen. For instance, nitrogen forms different combinations with oxygen and it is possible therefore to form $NO_x$. Sometimes, nitrogen will also form preferentially $NO_2$ but this is not the only form of $NO_x$ which can be formed. Another form of nitrogen is nitrosodioxyl radical (ONOO). This radical is not the only nitrogen based radical which may be formed alternative to various oxides of nitrogen. Accordingly, these form what might be known as oxides of nitrogen generally, and they are all collectively hydrophobic in reaction with the hydrophobic membrane of the present disclosure. In a process which forms oxides of nitrogen, it is not uncommon to also form or to have available traces of oxides of sulfur which again take the form of $SO_x$. These and other hydrophobic gases can be detected through the use of an appropriate detector. They have a similar reaction to the present reaction described for oxides of nitrogen generally speaking, and in particular nitric oxide which is probably the most common of the oxides of nitrogen. Accordingly, hydrophobic gases in general includes oxides of sulfur which also cooperate with the porous membrane described in the present disclosure.

BRIEF DESCRIPTION OF THE DISCLOSED APPARATUS

The present disclosure in one embodiment utilizes a two position, six port valve. In one position there is a helium flow path which includes a needle valve which provides a controllable measure of resistance to helium flow. Helium is the preferred carrier gas. Moreover, the six port, two position valve has a flow path which connects into a tubing segment located within a sample receiving container. This tubing segment is formed of a hollow tubing material which is hydrophobic in nature. It is located within a container receiving the sample and the sample is stirred in the container. Stirring the sample enables enhanced contact between trace gases dissolved in the sample solution. The trace gases infiltrate the wall of the tubing. The sample valve is switched periodically at a fixed rate. The needle valve is adjusted to provide a resistance to flow which is equal to the resistance to flow through the hydrophobic tubing. When switched, the carrier gas flow continues, but switching directs it into the hydrophobic tubing thereby picking up the molecules of the trace gases in the porous wall of the tubing. This concentrates the trace gases which are then carried by the flow of the carrier gas, helium in the preferred embodiment, which then is directed by a vacuum pump into a gas analyzer which detects the presence of NO. This appears to concentrate the NO by a large scale factor such as ten fold, easily one hundred fold, and perhaps as much as one thousand fold, and that transmits the peak to the analyzer. The analyzer detects and records the passage of the peak and provides an output which quantifies the concentrated NO.

The described and illustrated embodiment of bound nitrogen detector responds to NO and other $NO_x$ gases.

Generally it will recognize many types of oxides of nitrogen. If desired, it is also possible to test for oxides of sulfur using a bound sulfur analyzer. Accordingly, the analyzer which is connected to the present apparatus preferably handles the designated oxides of nitrogen or oxides of sulfur.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
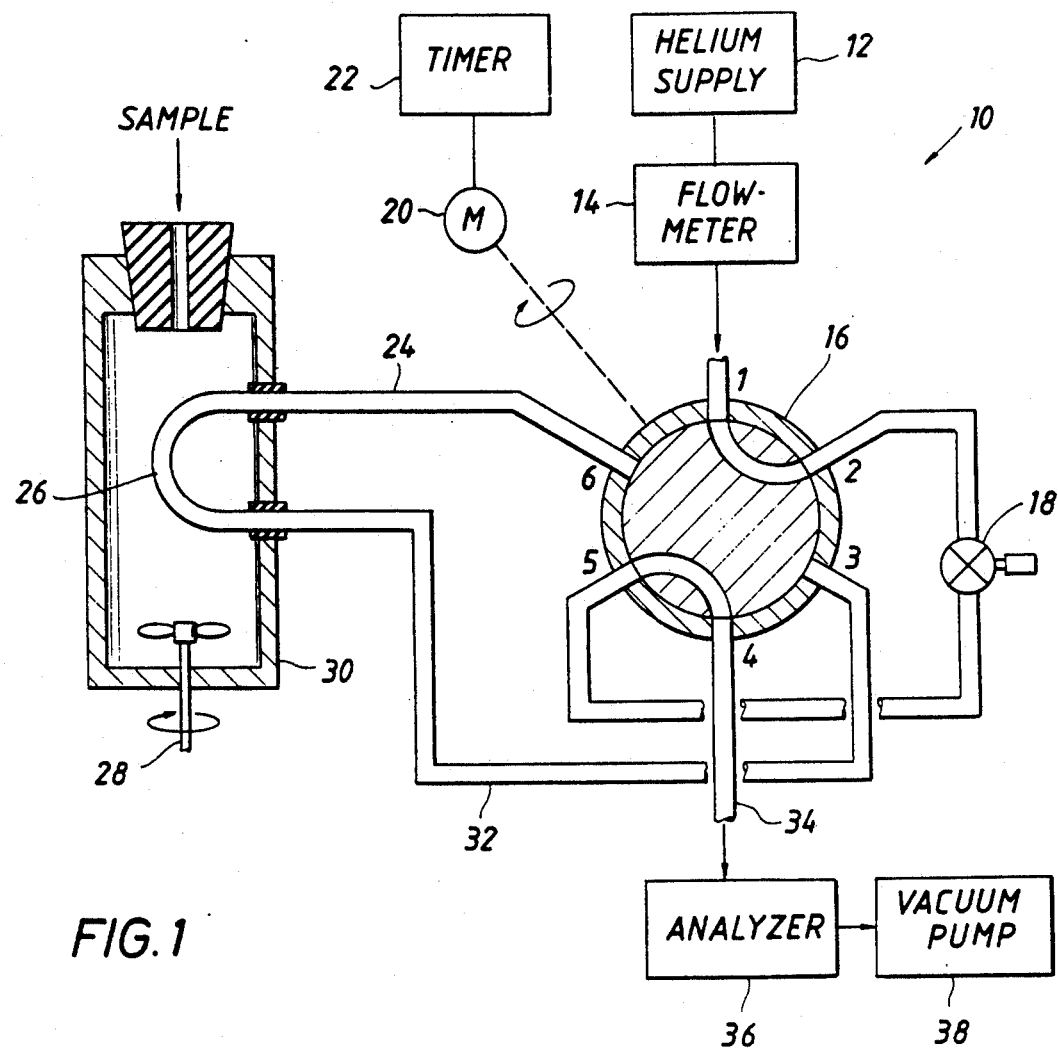
FIG. 1 shows a system involving a hydrophobic tubing which is exposed to an aqueous solution permitting absorption of hydrophobic molecules into the wall of the tubing which is periodically swept to deliver the necessary carrier gas and hydrophobic gases to responsive to the gases.

Attention is first directed to FIG. 1 of the drawings where the numeral 10 identifies a system which accomplishes hydrophobic gas testing in accordance with the present disclosure. The analytical system 10 will be described in the context of a system which responds to oxides of nitrogen. If desired, an alternate detector can be used which responds to oxides of sulfur. As defined herein, other detectors for hydrophobic gases can likewise be used. The apparatus of the system will be described first and then the methods of the present disclosure will be given. The system utilizes a flow of helium which is provided by a helium supply 12. The supply is connected with a flow meter which regulates the flow of helium gas. The flow meter 14 is connected to the first port of a six way valve 16. A representative six way valve is provided by Valco Instruments Company of Houston, Texas. There is one flow path through the system which involves the introduction of carrier gas through the first port and it then flows out through the second port into a needle valve 18. The needle valve 18 is connected between ports 2 and 5 as illustrated. The needle valve 18 is adjustable to provide a specific resistance to carrier gas flow. This resistance to gas flow is adjustable. It is adjusted to a level so that there is no bump or change in carrier gas flow observed at the NO test instrument down stream of the equipment as will be described in detail. Suffice it to say, the needle valve 18 is connected between ports 2 and 5 of the valve 16. For controlled operation, the valve 16 is switched by means of a motor. To this end, a motor 20 is connected with the valve for switching it between the two operative positions. In the illustrated position the first and second ports are connected through the valve rotor while ports 4 and 5 are also connected through the valve rotor. As will be detailed these are switched on timed movement of the valve to the switched position. The motor 20 is connected to a timer 22 which controls periodic operation of the motor so that it is switched periodically, for instance, once per minute, perhaps once every ten minutes, etc. This is a scale factor that will be discussed in detail.

In addition, port 6 is connected by means of a line 24 to a tubing segment 26 which is formed of a hydrophobic material. A stirring device 28 is located within a container 30. This is the sample container which is filled with a sample in aqueous solution. The sample container is preferably filled and plugged so that atmospheric gases do not commingle with the sample. The segment 26 is hydrophobic material as mentioned. It has a specific wall construction which is permeable to certain sized molecules. As a generalization, the microscopic pathways which comprise the pathway through the wall of the hydrophobic material permit passage of oxides of nitrogen and oxides of sulfur. Other hydrophobic gases may also migrate through the passages which migration is generally dependent on the relative size of the pores in the membrane and also on the mobility of the hydrophobic gas molecule with respect to the pores through the wall. These molecules are able to migrate through the tubing 26. The NO molecules in the solution in the container 30 are therefore able to migrate into, partially or completely through the wall, and are thereby separated from the aqueous solution. The tubing is made of a hydrophobic material which is permeable to oxides of nitrogen. The tubing is in the range of about 0.002 to 0.25" diameter and has a wall thickness of up to about 0.003".

Another tubing segment 32 connects down stream from the tubing 26 to the third port of the valve 16. This port is controllably switched and connected to the fourth port on switching; as illustrated presently, the flow of carrier gas is introduced through the first port and goes out through the second port, encounters a controlled pressure drop at the needle valve 18, then is reintroduced into the port 5 and flows out of the fourth port. The line 34 extends to a vacuum pump which delivers the carrier gas along with the necessary sample gas to an analyzer for NO. One suitable brand of NO detector is manufactured by Antek of Houston, Texas. It is also described by the Parks patent mentioned above. The detector is responsive to bound nitrogen and hence is able to recognize all types of oxides of nitrogen including NO, $NO_2$, $NO_x$, ONOO, and so on. That firm also provides an analyzer which is responsive to oxides of sulfur. That enables detection of sulfur based hydrophobic gases. Moreover, the system of the present disclosure preferably operates in a bumpless mode meaning it is operated so that switching of the valve does not provide a change in gas flow as observed at the analyzer. FIG. 1 thus shows the vacuum pump and analyzer connected to the line 34, the analyzer 36 being provided with the flow of carrier gas from the pump 38.

Consider a sequence of operation which may describe certain advantages of the present apparatus. Assume that a biological sample is obtained which has an extremely small trace quantity of NO and other gases in it. If desired, the test can be limited solely to oxides of nitrogen; in that instance, the output data will represent the nitrogen based compounds which migrate through the porous barrier. For simplicity sake in this description, it is assumed that NO is the only hydrophobic nitrogen based compound present. The sample is introduced in the aqueous solution form into the container 30. The container 30 is closed to avoid absorption of stray gases from the atmosphere. The flow of carrier or sweep gas through the system begins with the supply of carrier gas 12, helium being the preferred form. Alternately, other inert gases can be used such as argon. The supply 12 is operated so that a regulated flow from the flow meter 14 is input to the valve 16. The regulated flow is directed through the needle valve 18 which provides a fixed amount of resistance to the flow which is adjusted and left at a particular setting once the system is installed. That setting is adjusted so that there is no change in flow at the vacuum pump 38 on switching the valve 16. In any case, the carrier gas is introduced as mentioned and flows through the needle valve 18 and is then routed through the appropriate ports to the vacuum pump 38 and the analyzer 36 in the illustrated connection. When switched, the helium flow is directed into the valve 16 at the first port and then flows out of the valve 16 through the tube 24, then through the tube 26 and back through the tube 32 and is input to the valve 16. It is routed then by the valve through the outlet line 34 and to the analyzer 36. In the latter route, the switched flow of gas is directed through the hydrophobic wall tubing 26. The helium will pick up the molecules of NO in the hydrophobic material. When this occurs, the gas from the liquid sample is transferred in the form of a concentrated peak to the NO analyzer. The analyzer forms an output indicative of the chemically bound nitrogen which, in this instance, is only NO.

Figure 2:
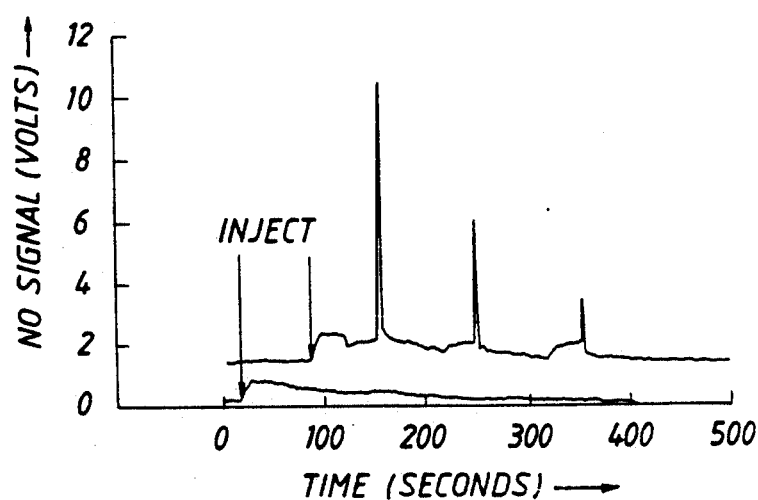
FIG. 2 is a graph showing one curve derived from continuous measurement of NO in contrast with the peaks arising from switched operation as taught by the present disclosure.

FIG. 2 of the drawings shows two curves derived over 500 seconds. The output signal of the analyzer 36 is the ordinant. The smaller curve shows the output voltage which is less than about one volt where continuous measurement is made while directing the carrier gas through the tubing 26. In this instance, an aqueous solution having a 1 micromolar solution of NO is injected into the container 30. The smaller curve shows the difficulty in obtaining a substantial voltage output signal. By contrast, with pulsed periodic operation occurring every 60 seconds where the valve 16 is switched in an on/off cycle of about 20/40 proportioning, it will be observed that peaks are formed in the output signal. The peaks are from the same sample concentration. They are peaks because there is an interval during which the NO is able to be absorbed into the hydrophobic material making up the tubing wall. As mentioned earlier, the hydrophobic material is permeable enabling migration of a number of nitrogen based oxides which may be detected assuming others are present. If only NO is present, then the response will be unique to NO.

The several peaks shown in FIG. 2 of the drawings form signals which can be scaled depending on the settings of the equipment such as gas flow rate, tubing diameter, wall thickness, etc. so that useful data can be obtained. Peak amplitude can be correlated to peak solution by the following relationship:

$$[NO]_s = [NO]_p \frac{1}{1 - e^{k1 \Delta t}}$$

In the foregoing equation, the NO solution concentration on the left side of the equation is given by the peak measurement which is on the right side of the equation. The exponential incorporates a constant of proportionality and is a function of the time interval over which the NO is permitted to accumulate in the wall of the membrane. The foregoing equation was developed solely for NO; an equation of the same general form can be used for other nitrogen based oxides or oxides of sulfur. Likewise, it can be extended to other hydrophobic gases which are able to pass through the porous membrane.

While the foregoing is directed to the preferred embodiment, the scope thereof is determined by the claims which follow:

We claim:

1. A method of detecting trace quantities of oxides of nitrogen from a sample in solution comprising the steps of:
   (a) positioning a tube to pass through a container;
   (b) wherein said tube is constructed of a hydrophobic material which is permeable to oxides of nitrogen;
   (c) placing the sample solution in contact with said tube;
   (d) stirring the solution to enhance contact between the oxides of nitrogen and said tube;
   (e) permitting oxides of nitrogen in the solution to migrate from the solution into the tube;
   (f) switching a valve to obtain a pulsed, periodic flow of carrier gas through the tube so that oxides of nitrogen in the tube are removed by the flowing carrier gas; and
   (g) analyzing the carrier gas for concentration of oxides of nitrogen after the pulsed flow.

2. The method of claim 1 including valve switching carrier gas flow through two routes by valve switching so that both routes, when switched, provide constant gas flow for analyzing.

3. The method of claim 2 including the step of placing an adjustable gas flow means in one of the gas flow routes to vary and adjust gas flow to produce a constant gas flow for analyzing.

4. An apparatus for measuring trace quantities of oxides of nitrogen, comprising:
   a sample receiving container;
   a hydrophobic tube which is permeable to oxides of nitrogen having an inlet and an outlet wherein the tube extends through the container;
   a carrier gas source connected with the inlet of the tube, wherein the tube is filled with a carrier gas;
   means for injecting a sample containing oxides of nitrogen into the container;
   an analyzer for oxides of nitrogen connected to the outlet of the tube wherein the analyzer generates an electronic signal proportional to the quantity of oxides of nitrogen in the carrier gas;
   means for redirecting the flow of the carrier gas wherein the carrier gas can be redirected through a bypass around the tube to the analyzer; and
   means for adjusting the flow rate of carrier gas through the bypass wherein said analyzer receives a constant gas flow.

5. The apparatus of claim 4 wherein said sample receiving container holds an aqueous solution.

6. The apparatus of claim 5 wherein said sample receiving container includes means for stirring.

7. The apparatus of claim 4 further comprising a timer which activates the means for redirecting wherein the carrier gas flow is swept through the tube at timed intervals.

8. A method of measuring trace quantities of oxides of nitrogen in a sample of a pathological fluid comprising the steps of:

(a) positioning a tube to pass through a sealed container wherein the tube is made of a hydrophobic membrane which is permeable to oxides of nitrogen;
(b) filling the tube with a carrier gas;
(c) injecting a known volume of a sample solution containing oxides of nitrogen into the container wherein the sample solution is in direct contact with the outside surface of the tube;
(d) stirring the sample solution to enhance contact between the oxides of nitrogen and said tube;
(e) allowing the oxides of nitrogen in the sample solution to migrate through the membrane into the tube and concentrate in the carrier gas wherein the carrier gas is held stationary for a predetermined period of time;
(f) sweeping the carrier gas through the tube, wherein the oxides of nitrogen are delivered to an analyzer which generates a series of electronic signal peaks proportional to the quantity of oxides of nitrogen in the carrier gas;
(g) repeating steps d-e at fixed, pre-determined intervals of time.

9. The method of claim 8 wherein the sample being analyzed for oxides of nitrogen is blood-free.

10. The method of claim 8 wherein the sample is injected into an aqueous solution within the container.

11. The method of claim 8 including the step of providing a constant carrier gas flow to the analyzer wherein a valve switching means is used to bypass the tube and deliver carrier gas to the analyzer during the time interval between each sweep of carrier gas through the tube.

12. The method of claim 11 including the step of placing an adjustable gas flow means in the bypass to vary and adjust gas flow to produce a constant gas flow to the analyzer.

* * * * *

UNITED STATES PATENT AND TRADEMARK OFFICE
CERTIFICATE OF CORRECTION

PATENT NO. : 5,248,616
DATED : September 28, 1993
INVENTOR(S) : Joseph S. Beckman, et al.

It is certified that error appears in the above-indentified patent and that said Letters Patent is hereby corrected as shown below:

Column 1, line 10, replace "vasodilatory" with -- vasodilator --.
Column 1, line 37, replace "pathological" with -- physiological --.
Column 1, line 41, replace "pathological" with -- physiological --.
Column, 1, line 43, replace "pathological" with -- physiological --.

Signed and Sealed this

Nineteenth Day of April, 1994

Attest:

BRUCE LEHMAN

*Attesting Officer*    *Commissioner of Patents and Trademarks*